United States Patent [19]

Tolbert et al.

[11] Patent Number: 4,537,860

[45] Date of Patent: Aug. 27, 1985

[54] STATIC CELL CULTURE MAINTENANCE SYSTEM

[75] Inventors: William R. Tolbert, Manchester; Joseph Feder, University City; Charles Lewis, Jr., Hazelwood, all of Mo.

[73] Assignee: Monsanto Company, St. Louis, Mo.

[21] Appl. No.: 447,748

[22] Filed: Dec. 8, 1982

[51] Int. Cl.$^3$ .................. C12M 1/12; C12M 1/04; C12M 3/00; C12M 1/00; B07B 1/30; B07C 5/16; C12N 5/00; C12N 5/02

[52] U.S. Cl. .................. 435/240; 435/241; 435/284; 435/287; 435/311; 435/313; 210/342; 210/645

[58] Field of Search ......... 435/3, 240, 241, 284, 435/4, 287, 288, 289, 290, 311–315, 948; 422/48, 61, 68; 210/333.2, 342, 31.2, 645, 651

[56] References Cited

U.S. PATENT DOCUMENTS

| | | | |
|---|---|---|---|
| 3,154,487 | 10/1964 | Thorton et al. | 210/323.2 |
| 3,361,260 | 1/1968 | Buckman | 210/130 |
| 3,420,377 | 1/1969 | Vandersip | 210/315 |
| 3,524,552 | 8/1970 | Carmon | 210/342 |
| 3,672,509 | 6/1972 | Buchmann et al. | 210/321.2 |
| 3,997,396 | 12/1976 | Delente | 195/1.8 |
| 4,201,845 | 5/1980 | Feder et al. | 435/285 |
| 4,220,725 | 9/1980 | Knazek et al. | 435/285 |
| 4,266,032 | 5/1981 | Miller et al. | 435/241 |
| 4,293,654 | 10/1981 | Levine et al. | 435/241 |
| 4,307,193 | 12/1981 | Iizuka | 435/68 |
| 4,335,215 | 6/1982 | Tolbert et al. | 435/241 |
| 4,391,912 | 7/1983 | Yoshida et al. | 435/241 |
| 4,415,668 | 11/1983 | Siegel | 435/241 |

FOREIGN PATENT DOCUMENTS

| | | | |
|---|---|---|---|
| 2059436 | 4/1981 | United Kingdom | 435/240 |
| 2094832 | 9/1982 | United Kingdom | 435/240 |

OTHER PUBLICATIONS

McCabe et al., *Unit Operations of Chemical Engineering*, McGraw Hill Inc., 1976, pp. 124–130.

Strand et al., *In vitro*, vol. 18, No. 3, Pt. II, Mar. 1982, Abstract 151, p. 311, "Matrix Perfusion-Microcarrier Bead Culture of Anchorage Dependent Cells".

McCoy et al., *Proc. Soc. Exptl. Biol. Med.* 109, 235–237, (1962).

Davies, *Exptl. Cell. Res.* 134, 367–376, (1981).

*Primary Examiner*—Thomas G. Wiseman
*Assistant Examiner*—Robin Teskin
*Attorney, Agent, or Firm*—Scott J. Meyer; James W. Williams, Jr.

[57] ABSTRACT

A method and apparatus for maintaining animal cells in vitro in a substantially arrested state of proliferation with continuous secretion of cell product is disclosed. The cells are retained within a reactor vessel chamber in a semi-rigid matrix having interstices for passage of fluid nutrient medium. Fresh nutrient medium is supplied by perfusion into the matrix through relatively low porosity tubes which are suspended in the reactor chamber and which substantially traverse the matrix; expended medium and cell product is withdrawn through relatively high porosity tubes which also are suspended in the reactor chamber and which substantially traverse the matrix; and oxygenated gaseous medium is supplied by perfusion into the matrix through a selectively-permeable membrane disposed in the reactor chamber.

9 Claims, 5 Drawing Figures

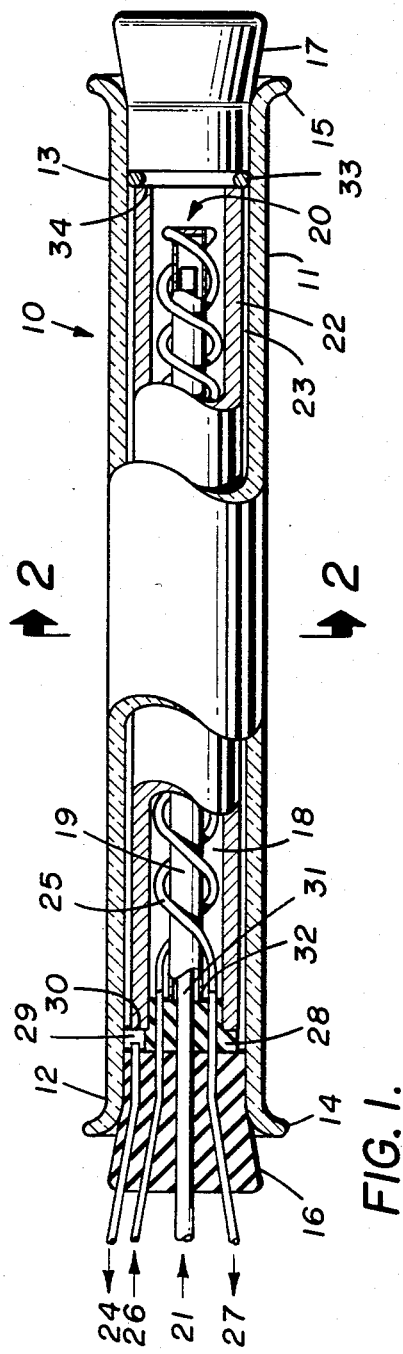
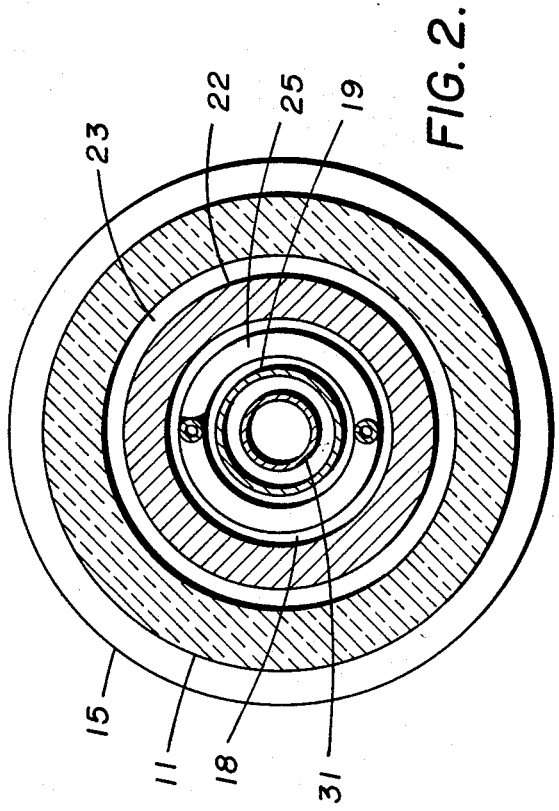

BRIEF DESCRIPTION OF FIGURES

FIG. 1 is a side elevation view partly in cross-section showing one embodiment of the static cell culture reactor vessel of the invention.

FIG. 2 is an end view taken along the line 2—2 of FIG. 1.

DETAILED DESCRIPTION OF FIGURES

Figure 3:
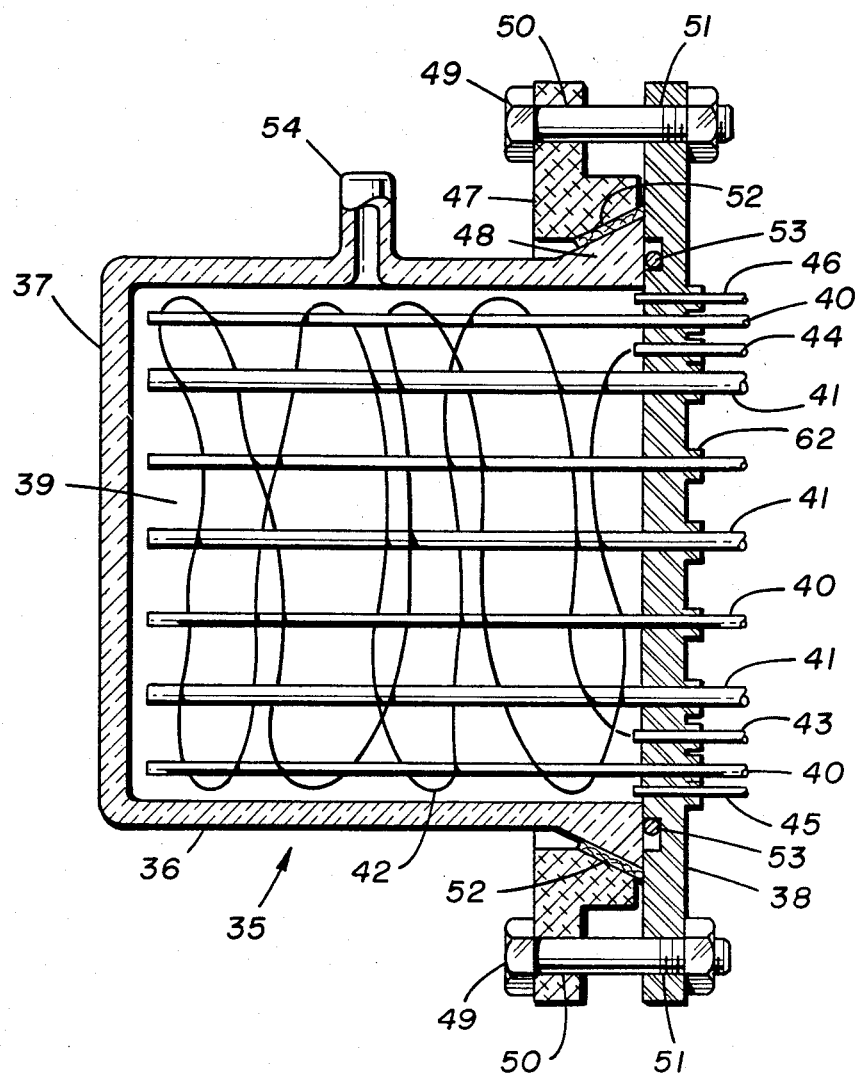
FIG. 3 is a side elevation view partly in cross-section showing another embodiment of the static cell culture reactor vessel of the invention.

Now with particular reference to the embodiment shown in FIGS. 1 and 2, reference numeral 10 refers generally to a cell culture reactor vessel which can be used for the static maintenance of mammalian and other animal cells. The reactor shell preferably is made of clear glass or non-toxic rigid plastic materials but also can be made of biocompatible metals such as, for example, stainless steel. The reactor is shown to have a generally cylindrical shell with sidewall 11 and openings at opposite ends 12 and 13. The cylindrical sidewall can be provided with flared edges 14 and 15 to accomodate wires (not shown) or other such means for reactor support or closure retention purposes. The ends of the cylindrical vessel are shown to be closed with elastomeric stoppers 16 and 17. Stopper 16 is provided with four holes for placement of rigid feed and exhaust tubes into the reactor at one end 12 to serve as inlet and outlet ports for fluid medium and gases. Arrows indicate the preferred direction of flow through these inlet and outlet ports during operation of the reactor. The other reactor end 13 can be permanently sealed but is shown in FIG. 1 to be provided with a stoppered opening as a matter of convenience for additional access to the reactor chamber 18 during downtime of the apparatus. If end 13 is permanently sealed, an alternate opening (other than at end 12) would be preferred for initial packing of the matrix and cells into the reactor chamber. During operation of the reactor vessel, end 13 should be closed.

The reactor 10 is structured to accomodate within its interior chamber 18 a semi-rigid matrix having interstices for retaining cells and for passage of fluid nutrient medium. In order to supply nutrient medium to the cells, a first porous tube 19 which is open at its proximal end and in fluid communication with external inlet port 21 is centrally disposed in the matrix zone substantially throughout the entire length of said zone. Porous tube 19 is closed at its distal end 20 but this closure can have the same porosity as the sideway of tube 19. The pore size of tube 19 should be such as to permit perfusion of nutrient fluid through its porous walls into the matrix. A porous porcelain tube, a porous cellulose, polytetrafluoroethylene, or polysulfone hollow capillary membrane tube, or other such porous tube having a relatively small pore size of from about $0.2\mu$ to about $5\mu$ is preferred to establish a pressure drop across the tube wall to enhance uniformity of medium distribution. Smaller pore sizes, even as low as about $0.01\mu$, can be used but are less preferred due to the tendency to clog if particulate matter in excess of such pore size is present in the fresh nutrient medium.

A second porous tube 22 which is concentric to and envelopes porous tube 19 also is disposed substantially throughout the entire length of the matrix zone. Tube 22 can be closed at its distal end but preferably is open for convenient access to the matrix zone through reactor end 13 during downtime of the apparatus as stated hereinbefore. The outer diameter of tube 22 is slightly less than the inner diameter of the reactor shell to provide an annular channel 23 for passage of expended (spent) media and cell product through external outlet port 24. The pore size of tube 22 should be larger than the pore size of tube 19 and, preferably, also has a larger surface area to facilitate removal of spent media and biomolecular cell products from the reactor vessel. A porous porcelain tube or other such porous tube having a relatively large pore size of from about $10\mu$ to about $150\mu$ is preferred. This larger pore size and surface area minimizes the pressure drop across the exit tube. The semi-rigid structure of the matrix and maintenance of a relatively low flow rate in the nutrient medium tends to prevent cells from migrating through the high porosity tube 22.

It will be appreciated that the relative positions of the first and second porous tubes can be reversed such that the second porous tube 22 is the low porosity tube and the first porous tube 19 is the high porosity tube. In such configuration, port 24 will be a fluid medium inlet port and port 21 will be a fluid medium outlet port.

It is preferred that the maintenance reactor 10 be operated in a generally horizontal position with the effluent outlet port 24 being positioned near the top of the reactor. In FIG. 1, the reactor is shown in a generally vertical orientation when the drawing sheet is held in an upright position for the clearest illustration of the invention due to the extended length of the reactor relative to its diameter.

In order to supply oxygenated gaseous medium to the cells, a selectively-permeable tubular membrane 25 also is disposed substantially throughout the entire length of the matrix zone. Membrane 25 should be gas-permeable, substantially liquid impermeable; such properties can be provided by silicone rubber tubing, e.g., Dow-Corning Silastic ® medical grade tubing. Silicone rubber tubing of about one mm inside diameter and about 2 mm outside diameter is preferably used. In the embodiment shown in FIGS. 1 and 2, a single length of tubular membrane 25 is coiled around porous tube 19. Tubular membrane 25 is shown to be attached at its ends to rigid tubes 26 and 27 which constitute, respectively, the gas inlet and outlet ports through stopper 16.

To provide desirable spacing and support for the porous tubes 19 and 22 and the tubular membrane 25 within the reactor interior, a silicone rubber septum 28 is positioned close to the reactor end 12 and adjacent to the inner side of stopper 16. Septum 28 is provided with four holes which coincide with the four holes in stopper 16. A notch 29 provided in the outer periphery of the septum facilitates collection of effluent from the annular channel 23 through external outlet port 24. The peripherally flanged portion of the septum is adapted to receive the annular proximal end 30 of porous tube 22. The septum also provides a fluid sealing relationship between the external effluent and internal matrix zones.

Additional support for porous tube 19 is provided by a stainless steel tube 31 which is inserted through external inlet port 21 of stopper 16 and disposed lengthwise

STATIC CELL CULTURE MAINTENANCE SYSTEM

BACKGROUND OF THE INVENTION

This invention relates to a method and apparatus for cell culture and more particularly to a static cell culture maintenance system.

The culture of animal cells in vitro for the production of various proteins, peptides, hormones, growth factors and other biologically active substances has been widely investigated. A great many animal cells have been utilized in cell culture to secrete important biomolecules which are of significant biomedical interest. For example, pituitary cells have been cultured in vitro to produce growth hormone; kidney cells have been cultured to produce plasminogen activator; and hepatitis-A antigen has been produced in cultured liver cells. Other cells have been specifically cultured to produce various viral vaccines and antibodies. So also, interferon, insulin, angiogenic factor, fibronectin and numerous other biomolecules have been produced by the in vitro culture of various animal cells.

A great diversity of procedures and apparatus for in vitro cell culture production of biomolecules of interest has been utilized heretofore. In certain relatively simple systems, the cells are grown to confluence in tissue flasks and roller bottles in the presence of suitable nutrient media. More complex systems have utilized capillary hollow fiber membranes as the surface support and as the means of supplying nutrient media to the cells. In the latter systems, nutrient culture media can be pumped through the lumen of hollow fibers arranged in an elongated bundle as described in U.S. Pat. Nos. 3,821,087; 4,220,725; and 4,184,922; or oxygen can be supplied through the hollow fiber membranes to maintain aerobic conditions as disclosed in U.S. Pat. No. 3,997,396.

A further improvement of the hollow fiber membrane cell culture technology employs a flat bed configuration in which the nutrient medium is supplied transverse to the bed of fibers in a relatively short flow path as seen from U.S. Pat. Nos. 4,087,327 and 4,201,845. The flat bed configuration reduces the undesirable nutrient gradient produced by the elongated cartridge or bundle configuration of the hollow fiber membranes.

Other cell culture systems propagate the cells in agitated liquid suspension culture, particularly for larger scale operations as described, for example, in U.S. Pat. Nos. 4,059,485; 4,166,768; 4,178,209; and 4,184,916. In the case of cells which require surface support, microcarriers have been employed in the suspension culture medium as the support means. Such microcarriers are illustrated, for example, in U.S. Pat. Nos. 3,717,551; 4,036,693; 4,189,534; 4,203,801; 4,237,033; 4,237,218; 4,266,032; 4,289,854; 4,293,654; and 4,335,215.

Further background information on conventional culture conditions for the production of animal cells in microcarrier culture can be had by reference to the recent paper by Clark and Hirtenstein, *Ann. N.Y. Acad. Sci.* 369, 33-45 (1981).

In most of the aforesaid in vitro cell culture systems, emphasis has been placed on means to stimulate proliferation of large numbers of cells or for investigation of differentiated function of very few non-proliferating cells. Although some secreted biomolecules can be produced during periods of high proliferation, more efficient production of such export biomolecules can be obtained in arrested, more differentiated states. Moreover, some in vivo secretory cells have very low proliferation rates. Accordingly, an in vitro cell culture system which allows a large number of cells to be maintained in a state of low proliferation but with continuous product secretion would be of significant value.

BRIEF DESCRIPTION OF THE INVENTION

In accordance with the present invention animal cells are maintained in vitro in a substantially arrested state in proliferation with continuous secretion of cell product by a system which comprises:

(a) suspending said cells in a semi-rigid matrix disposed in a cell culture reactor chamber and having interstices for passage of fluid nutrient medium, (b) supplying fresh nutrient medium for said cells by passing said nutrient medium through an external inlet in the reactor into the lumen of at least one first porous tube disposed in said chamber substantially throughout the expanse of said matrix and perfusing said nutrient medium through the walls of said porous tube into said matrix, (c) withdrawing expended nutrient medium and cell product from said matrix by perfusing through the walls of at least one second porous tube disposed in said chamber substantially throughout the expanse of said matrix and passing said spent medium and cell product through an external outlet in said reactor, said second porous tube having a pore size larger than the pore size of said first porous tube, and (d) supplying oxygenated gaseous medium for said cells by perfusing into said matrix through the walls of at least one selectively-permeable tubular membrane disposed in said chamber substantially throughout the expanse of said matrix and having openings at both ends of its lumen for inlet and outlet of said gas to and from the outside of said reactor.

The apparatus used in this cell maintenance system comprises a housing, a chamber within said housing for holding cells in a semi-rigid matrix with interstices for passage of fluid culture media, external culture medium inlet and outlet means disposed in a wall in said housing, said inlet means being in fluid communication with at least one relatively low porosity tube disposed substantially throughout the expanse of said chamber, said outlet means being in fluid communication with at least one relatively high porosity tube disposed substantially throughout the expanse of said chamber, external gas inlet and outlet means disposed in a wall in said housing and in gaseous communication with a selectively-permeable membrane disposed substantially throughout the expanse of said chamber, said relatively low and relatively high porosity tubes having closures at their ends which are distal to the external culture medium inlet and outlet means.

DETAILED DESCRIPTION OF THE INVENTION

While the specification concludes with claims particularly pointing out and distinctly claiming the subject matter regarded as forming the present invention, it is believed that the invention will be better understood from the following description of the preferred embodiments taken in connection with the accompanying drawings in which:

flanged end 48 and a set of fasteners 49 equidistantly spaced apart circumferentially through holes 50 in the bracket and holes 51 in the periphery of the endplate (e.g., nut and bolt assemblies as illustrated). An annular fibre cushion 52 is shown to be positioned intermediate the bracket and the reactor vessel to prevent breakage of a glass reactor wall from the sealing pressure of a metal bracket in the illustrative embodiment. An elastomeric O-ring seal 53 positioned between the lip of the flanged reactor end 48 and an indentation of the endplate 38 provides a fluid sealing relationship between the endplate and the reactor interior upon closure with fasteners 49. An optional port 54 can be positioned in the sidewalls 36 for removal of air bubbles.

Figure 5:
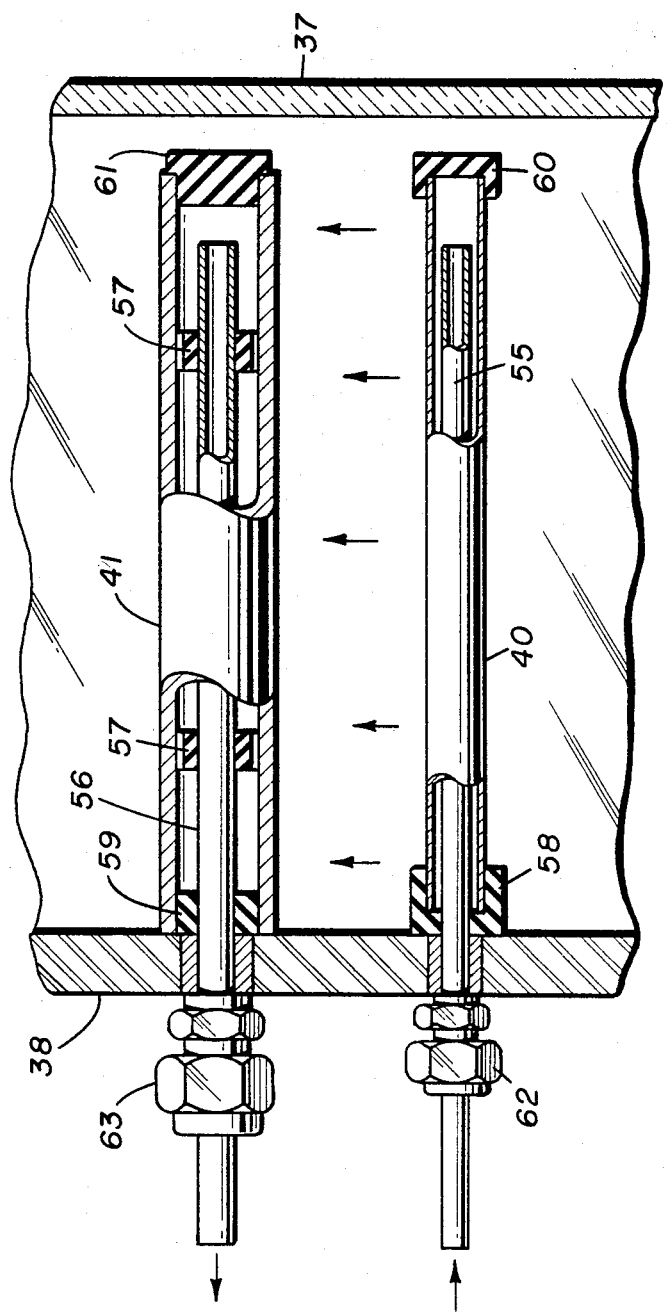
FIG. 5 is an enlarged side elevation view partly in cross-section showing a portion of the culture reactor vessel of FIG. 3 with a pair of inlet and outlet porous tubes in greater detail.

FIG. 5 shows one pair of the porous tubes 40 and 41 in greater detail. Arrows indicate the preferred direction of fluid flow of nutrient medium through these tubes and the matrix zone during operation of the reactor. In this enlarged view, the porous tubes 40 and 41 are shown to be supported with rigid tubes 55 and 56, respectively, which can be fabricated of stainless steel or other such rigid material. These rigid tubes are inserted through openings in the endplate 38 and disposed lengthwise into the porous tubes. The length of tubes 55 and 56 extending into the reactor interior is shorter than tubes 40 and 41 to permit the fresh nutrient and expended medium to flow around the distal end of the rigid tubes. Alignment of the high porosity tube 41 with rigid tube 56 is facilitated by silicone rubber spacers 57 which are notched to permit passage of medium. Silicone rubber seals 58 and 59 are used to seal the porous tubes to rigid tubes 55 and 56. Silicone rubber seals 60 and 61 also are provided at the distal ends of tubes 40 and 41, respectively, to provide closures of these tubes. Alternatively, these closures can have the same porosity as tubes 40 and 41. Swagelok ® unions 62 and 63 are shown to be welded into the endplate 38 to seal the rigid tubes 55 and 56, respectively, and to facilitate convenient assembly of the reactor.

Figure 4:
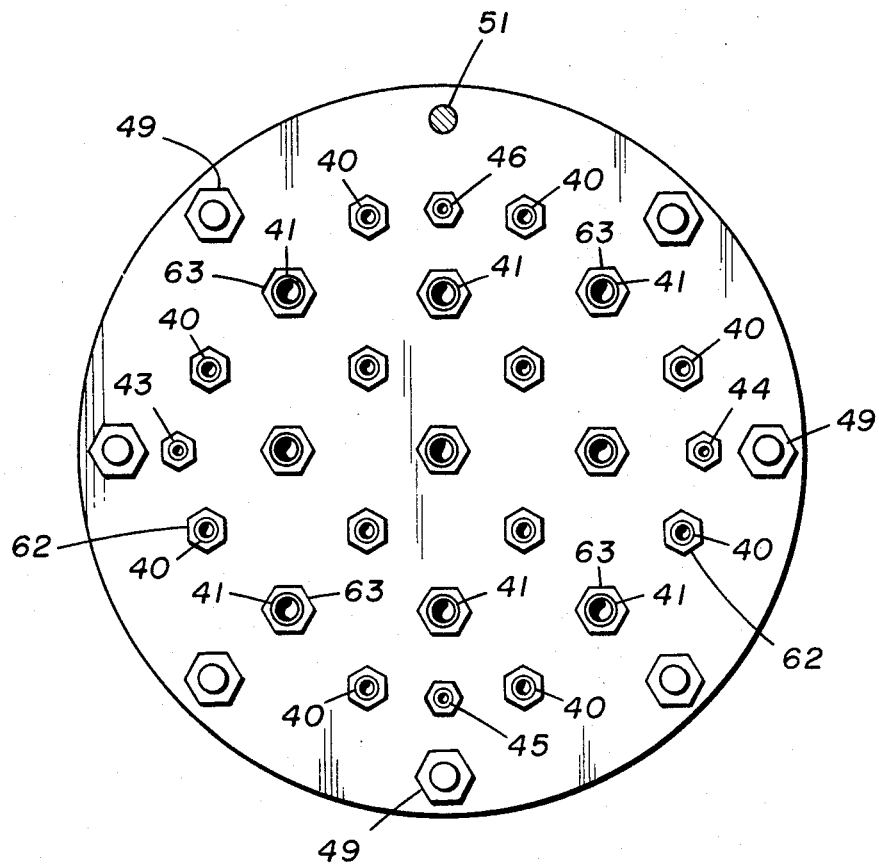
FIG. 4 is an end view of the embodiment shown in FIG. 3.

In order to illustrate the operation of the reactor vessel of FIGS. 3-5, cells are first grown in a separate vessel or cell culture system, e.g., the cell culture vessels and systems shown in U.S. Pat. Nos. 4,289,854 and 4,335,215, the disclosures of which are incorporated herein by reference. Cells can be attached to microcarriers (e.g., human diploid fibroblast cells such as FS-4 or AG1523 cells) or free (e.g., SK-HEP-1 human liver adenocarcinoma cells or hybridoma cells). These cells are then mixed at high concentration (e.g., 10 to 200 ml packed cells per liter) with a matrix material (e.g., Sephadex G-10, G-25 or G-50 beads). The cell-matrix slurry is then pumped into the reactor vessel 35 through inlet port 45 to completely fill the interior chamber 39 of the reactor. Excess fluid can be allowed to empty through the low porosity perfusion tube 40 and discarded. If sufficient cell-matrix slurry to fill the reactor interior is not available, additional matrix slurry can be pumped into the vessel through upper port 46. After filling and settling of matrix, additional matrix is again pumped-in through port 46 to completely fill the reactor.

Before normal operation of the maintenance reactor is instituted, the inlet port 45 preferably is disconnected from the cell-matrix supply source and a reverse flow of fresh medium from the high porosity tubes 41 to the low porosity tubes 40 is instituted to remove unattached cells from the immediate vicinity of the high porosity tubes. During operation of the maintenance reactor vessel, fresh medium is pumped directly or through a manifold from a fresh medium reservoir (not shown) into the low porosity tubes 40. The pressure drop across the low porosity tubes caused by this fresh medium flow maintains uniformity of perfusion throughout the reactor. Effluent product flows from the cell-matrix into the high porosity tubes 41 and out into a product/effluent reservoir (not shown). The pumping of medium during operation of the reactor can be carried out continuously or periodically at a flow rate sufficient to provide the nutrients required for survival of the particular cells being maintained in the reactor and to remove the cell product.

Cells can be maintained in this system for long periods of time with product continually harvested from the spent medium. In a 6-inch long, 6-inch diameter cylindrical reactor vessel, cells from 100 to 400 liters of conventional suspension culture can be maintained. In a 32-inch long, 6-inch diameter cylindrical reactor vessel, cells from 500 to 2000 liters of conventional suspension culture can be maintained.

While horizontal alignment of the reactor vessel allows extension of the length without changing perfusion parameters, other geometries of the system can be utilized. For example, the cylinder can be very large in diameter and relatively short in length (or width) but stand in a vertical position. It is preferable to minimize the hydrostatic pressure effects in the perfusion tubes so as to prevent non-uniformity of medium perfusion.

The apparatus of this invention can also employ auxiliary features such as, for example, pH and dissolved oxygen sensing electrodes, sampling ports, in-line air filters and the like cell culture system features.

The following detailed examples will further illustrate the use of the above-described static cell culture maintenance system although it will be understood that the invention is not limited to these specific examples.

EXAMPLE 1

A micro-static maintenance reactor (M-SMR) was constructed as shown in FIGS. 1 and 2. The reactor consisted of a Pyrex ® outer cylindrical shell about 6.5 inches long and 1 inch outside diameter and contained single high and low porosity tubes. The high porosity tube was about 5 inches long with three-fourths inch outside diameter and one-eighth inch wall thickness. This tube had a nominal pore size of 20 microns (Kynar porous-plastic tubing from Portex Technologies, Division of Glass Rock, Medical Services, Fairburn, GA 30213). Contained within the high porosity tube was a low porosity tube with 7/32-inch OD and 1/32-inch wall thickness. This microporous porcelain tube had a porosity of nominally 0.8 microns and was purchased under catalog #105779-04 from Selas, Flotronics Division, Huntingdon Valley, PA 19006. Approximately 24 inches of medical-grade silicone rubber tubing 1 mm ID and 2 mm OD were wrapped around the inner porous tube. This tubing was purchased under catalog #518-145 from Patter Products, Inc., Beaverton, MI 48612. The working volume of this reactor between the inner and outer porous tubes was approximately 10 ml.

The cells used in this run were an anchorage-independent hybridoma cell line designated 1-15 2F9 and developed by R. Kimes and J. Olander of Monsanto Company. This mouse-mouse hybridoma produces an IgG monoclonal antibody against an antigen associated with a human hepatoma cell line (SK-HEP-1). Background information on the illustrative SK-HEP-1 cell into tube 19. The length of tube 31 extending into the reactor interior should be shorter than tube 19 to permit the incoming nutrient medium to flow around the distal end of tube 31 and reach the entire inner periphery of the concentric porous tube 19. Spacing for tube 19 can be maintained by sealing it to tube 31 at proximal end 32. Positioning of an elastomeric O-ring seal 33 between the distal end 34 of tube 22 and elastomeric stopper 17 provides a fluid sealing relationship between interior chamber 18, annular channel 23 and stopper 17. Wires (not shown) or other such retaining means can be placed around flared edge 15 and stopper 17 to further facilitate such fluid sealing relationship.

The semi-rigid matrix can consist of any finely divided, non-toxic solid material which can be packed into the reactor chamber to retain the animal cells in a relatively static or fixed position within the interior of the reactor vessel and which provides interstices to permit passage of fluid nutrient medium through the matrix. Glass or silica beads, polymeric gel filtration beads such as Sephadex ® cross-linked dextran and Bio-Gel ® polyacrylamide beads, and cell culture microcarrier beads such as DEAE-Sephadex, Cytodex ® charged dextran, and Bio-Carrier ® acrylamide beads are examples of suitable matrix materials which are commercially available. The U.S. patents cited under the Background of the Invention, above, further describe other such well known microcarriers which are suitable for use in the present invention. The preferred microcarriers are polymeric, generally spherical particles having a diameter of from about $30\mu$ to about $400\mu$.

In the method of the present invention illustrated by the embodiment shown in FIGS. 1 and 2, nutrient medium is supplied through external inlet port 21 into the lumen of porous tube 19. The nutrient medium can be conveniently pumped from a fresh medium reservoir (not shown) as desired. The fresh medium perfuses through the porous walls of relatively low porosity tube 19 into the semi-rigid matrix which contains the desired animal cells interspersed between microcarriers or other such finely divided materials which constitute the matrix. By such means, the entire nutrient medium makes cell contact prior to exiting the reactor chamber through porous tube 22 and outlet port 24. This is distinguished from conventional flow-through hollow fiber membrane devices wherein only a portion of the nutrient medium diffuses through the membrane wall to reach the cells and the remainder passes through the continuous hollow fiber lumen to the outlet port at the other end of the device.

The cells and microcarriers can be initially charged into the interior chamber 18 of the reactor vessel through end 13 by removal of stopper 17. Prior to introduction into the cell culture maintenance reactor of this invention, the cells can be propogated by conventional means such as, for example, suspension culture or microcarrier attached suspension culture in separate cell proliferation systems. The individual cells or the cells attached to the microcarriers are concentrated, mixed with matrix material and then introduced into the static maintenance reactor vessel of this invention.

Oxygenation or aeration of the cells is achieved by circulating oxygen, air or other such oxygenated gaseous medium through selectively-permeable membrane 25. Spent medium and cell biomolecular product then exits the reactor vessel by perfusion through the porous wall of the relatively high porosity tube 22, passage into annular channel 23 and withdrawal through external outlet port 24. The spent medium can be conveniently collected in an effluent reservoir (not shown), and cell product can then be isolated and purified from the spent medium as desired by conventional means such as, for example, adsorption, extraction, ion-exchange chromatography, immunoaffinity chromatography, gel filtration and electrophoresis.

FIGS. 3-5 show another embodiment of the static-cell culture maintenance reactor vessel. As distinguished from the embodiment of FIGS. 1 and 2, the reactor vessel in FIGS. 3-5 contains a plurality of both the first porous tubes and the second porous tubes. This embodiment thus is generally adapted to a larger scale operation than the former embodiment.

In FIGS. 3-5, reference numeral 35 refers generally to a static cell culture maintenance reactor vessel having a generally cylindrical shell with sidewall 36, an endwall 37 and a removable disc-shaped endplate 38. The reactor vessel 35 accommodates in its interior chamber 39 a semi-rigid matrix having interstices for holding cells and for passage of fluid nutrient medium. In order to supply fresh nutrient medium to the cells, a group of twelve relatively low porosity tubes 40 is provided. A group of nine relatively high porosity tubes 41 is provided for removal of spent medium and cell product. These tubes are closed at their distal ends (distal to endplate 38). They are arranged substantially in parallel relationship to each other in the matrix zone and preferably are spaced apart such that a spent medium tube is positioned within about 2 cm lateral distance from each fresh medium tube. A sufficient number of fresh medium tubes preferably are provided in the reactor vessel such that the major portion of the matrix volume will be within about 2 cm lateral distance from a fresh medium tube. A shorter lateral distance (less than 2 cm) between the fresh medium and spent medium tubes is preferred when hollow capillary membranes are employed as the porous tubes such as, for example, hollow fiber membranes having a diameter of from about 100 to 1000 microns. The porous tubes should extend substantially throughout the length of the matrix (or width in a vessel having a chamber diameter greater than its length).

To provide oxygenation or aeration of the cells, a length of selectively-permeable membrane tubing 42 is intricately wound around the porous fresh medium and spent medium tubes. Inlet and outlet ports for this tubing are shown, respectively, at 43 and 44. For clarity, only a few windings of the membrane are shown. In practice, more than two hundred linear feet of silicone rubber tubing per foot of reactor vessel length have been used. Oxygen or air is flowed through the silicone rubber tubing under pressure of from about 0 to about 20 lb/in$^2$ gauge (0 to about 1.5 K/cm$^2$) and allowed to diffuse through the walls of the tubing into the surrounding matrix zone. Preferably, no point in the matrix zone exists at a distance greater than about 2 cm, and more preferably less than about 1 cm, from the oxygen supply tube.

Introduction of the cells and matrix material into the interior of reactor vessel 35 can be had through a matrix inlet port 45 located near the bottom of the vessel. A matrix overflow port 46 is positioned near the top of the vessel. This port also can be used for introduction of additional matrix material after settling of material initially introduced through inlet port 45.

The removable endplate 38 of the reactor vessel is conveniently attached to the reactor vessel by a split-ring bracket 47 which encircles the reactor vessel at its used without antibiotics. A flow rate for liquid medium between 1.5 and 3 mls/min was used throughout the 62-day run. The average liquid flow rate, as measured every two days during sampling, was 2.18±0.38 mls/min. Both oxygen and carbon dioxide concentrations were measured in the gas before entering the reactor and after traversing the 110–120 ft. of silicone rubber tubing. A gas flow of approximately 10 ml/min was maintained throughout the SMR run with a pressure differential of approximately 2 lbs/in$^2$ across the reactor. Samples of gas were read in an IL blood-gas analyzer and indicated a continual depletion of oxygen and increase of $CO_2$ throughout the run. Oxygen consumption by the reactor determined both from the change in the 10 ml/min gas flow and in the change in the approximately 2 ml/min medium flow was an average of $2.1 \pm 0.08 \times 10^{-5}$ moles of oxygen/min. Similar calculations could not be made for the carbon dioxide due to the evolution of $CO_2$ from the bicarbonate buffer with change in pH across the reactor. However, $CO_2$ concentration ranged from about 45 mm Hg in the input gas to 60–70 mm Hg after traversing the reactor. Input gas levels were about 40–45 mm of Hg of carbon dioxide and 250–300 mm Hg for oxygen. After the initial 18 liters of serum-containing medium perfused through the reactor over approximately 6½ days, serum-free medium supplemented with 0.5 mg/ml bovine serum albumin, 0.5 μg/ml insulin and 0.5 μg/ml human transferrin and 5 nl/ml linoleic acid was used. This serum-free medium was perfused for 24 days; during the final 32 days the 6% fetal bovine serum supplemented medium was used. Oxygen consumption and $CO_2$ production, as well as pH levels, remained substantially constant throughout the entire two-month period.

During the two month run, samples were taken and assayed for angiogenesis factor and plasminogen activator. The assay for the angiogenesis factor was by stimulation of endothelial cell growth as described by J. V. Olander, J. C. Marasa, R. C. Kimes, G. M. Johnston and J. Feder, "An Assay Measuring the Stimulation of Several Types of Bovine Endothelial Cells by Growth Factors Derived from Cultured Human Tumor Cells," *In Vitro* 18, 99–107 (1982). Substantial levels of endothelial cell growth stimulatory activity were observed throughout the run with the highest value occurring after reintroduction of serum supplemented media. From about a 2-fold to a 5-fold increase in endothelial cell number was obtained in comparison to controlled media (fresh growth media unexposed to the cells) during the maintenance period.

Plasminogen Activator (PA) activity can be determined by the fibrin plate method of Astrup, *Arch. Biochem. Biophys.* 40, 346–351 (1952) and variations thereof as described, for example, in U.S. Pat. No. 3,778,352. In this general method, the plasminogen activator in a sample is determined by measuring the diameter of a clear radial diffusion zone in a gel plate or dish caused by fibrinolysis of a known amount clotted fibrinogen in the gel. Such a clearing zone assay was used to detect plasminogen activator in samples from the above run as follow: Sea plaque agarose was mixed with fibrinogen, thrombin and plasminogen and then poured into a large petri dish and allowed to gel overnight. Reaction between the thrombin and fibrinogen formed a fibrin matrix within the agarose gel. Five μl samples of conditioned media from the static maintenance reactor run were spotted on this gel along with varying known concentrations of a urokinase standard solution. The gel was incubated at 37° overnight. Any plasminogen activator in the samples would catalyze the production of plasmin from the plasminogen contained within the gel. Plasmin then dissolved the fibrin matrix forming a circular cleared zone around the sample spot. After incubation, the gel was stained with 0.1% amido black at room temperature for 2 hrs in a solution of 70% ethanol, 10% acetic acid, 20% water and then destained in the same solvent for one day. The diameter of cleared circular zones around sample spots was compared with similar zones around known concentrations of urokinase. Substantial levels of plasminogen activator activity were found during the entire 24 days of serum-free perfusion, but the levels detected during the perfusion period in the presence of fetal bovine serum generally were lower. Fetal bovine serum contains an inhibitor to PA activity which accounts for the reduced response in its presence.

Plasminogen activator activity on samples from the above run was further confirmed by the measurement of the release of $^{125}$I-fibrin in the modified fibrin dish assay method as described by Feder et al., *Biochem, Biophys. Res. Commun.* 83(3) 1164–1170 (1978).

Conditioned medium from both fetal bovine serum containing portions of the growth and serum-free portions of the reactor run was concentrated on an Amicon hollow fiber system to retain materials above 10,000 molecular weight. These concentrates can also be assayed for various other activites. Thus, these concentrates were found to have positive activity for vascular permeability factor according to the method described by Dvorak et al., *J. Immunol.* 122(1), 166–173 (1979).

It should be understood that all types of animal cells can be maintained by the method and apparatus of this invention such as, for example, mammalian, amphibian and avian cells. In addition to the cells illustrated in the foregoing Examples, other cells can be employed which are representative of hybridomas, primary cultures of normal and neoplastic cells, transformed and nontransformed animal cell lines, such as human lung fibroblast (WI-38) cells, rhesus monkey kidney (MK-2) cells, cervical carcinoma (HeLa) cells, baby hampster kidney (BHK-21) cells, simian virus 40 transformed 3T3 mouse embryo fibroblast (SV3T3) cells, chick embryo fibroblast cells, and the like. So also, the apparatus and method of the invention is adapted for use with any conventional cell nutrient medium such as, for example, Eagle's basal medium, Dulbecco's modified Minimum Essential Medium (MEM), Medium 199, RPMI 1640 medium and the like.

Still other embodiments and examples of the invention will be apparent to the person skilled in the art after reading the present disclosure without departing from the spirit and scope of the invention and it will be understood that all such further embodiments and examples are included within the scope of the appended claims.

What is claimed is:

1. A method of maintaining animal cells in vitro in a substantially arrested state of proliferation with continuous secretion of cell product which comprises:
   (a) suspending said cells in a semi-rigid matrix of finely divided particles disposed in a cell culture reactor chamber and having interstices for passage of fluid nutrient medium,
   (b) supplying fresh nutrient medium for said cells by passing said nutrient medium through an external inlet in the reactor into the lumen of at least one first porous tube disposed in said chamber substanline can be had by reference to U.S. Pat. No. 4,209,587, the disclosure of which is incorporated herein by reference. The hybridoma culture was grown to approximately $10^6$ cells/ml in a 500 ml conventional spinner and collected by gentle centrifugation at 200 rpm into the matrix material. This matrix material consisted of Sephadex ®G-50 chromatography beads which were sterilized by autoclaving in phosphate buffered saline (PBS) and washed with the nutrient medium used for perfusion in this Example. Dulbecco's modified MEM medium with 4.5 grams/liter glucose supplemented with 6% fetal bovine serum was used without antibiotics. The pellet of cells and chromatography beads was retained in the conical portion of a centrifuge bottle after aspiration of the supernatant. A dense slurry of cells and beads was then pipetted into the M-SMR device with removal of some bead-free effluent. This cell containing effluent was used to wash in more of the bead slurry. As the pore size of the high porosity tube was larger than the average size of the hybridoma cells, portions of these cells migrated through the walls of the high porosity tube into the effluent during the inoculation procedures. However, after sealing the reactor and initiating perfusion of nutrient medium, relatively few hybridoma cells were lost. While determination of exact values of the cell inoculum are not possible due to losses in centrifugation and through the high porosity tube, it is estimated that between $2 \times 10^8$ and $5 \times 10^8$ cells were retained within the 10 ml operating volume of the reactor. Viability of these cells by dye exclusion was estimated to be approximately 80%. Medium was perfused through the reactor at a rate of approximately 2 mls/hr and a gas mixture flowed through the silicone rubber tubing at a rate of 1-2 mls/min. This gas mixture consisted of carbon dioxide, oxygen and air such that average concentrations of the input gas were $37 \pm 12$ mm Hg carbon dioxide and $310 \pm 46$ mm Hg oxygen. These concentrations were measured in an IL blood-gas analyzer (Instrumentation Laboratories). During the two-week run of this reactor, samples were taken at 1-3 day intervals for measurement of pH and dissolved gas concentrations and also for determination of antibody levels. During the run, the average pH value was $7.13 \pm 0.11$, the dissolved $CO_2$ was $58.7 \pm 14$ mm Hg and the oxygen level was $116 \pm 13$ mm Hg. These results indicate that culture parameters were maintained within desired operating ranges during the entire growth period (desired pH between about 6.9 and 7.3; desired oxygen between about 20 mm Hg and 160 mm Hg; and desired $CO_2$ between about 35 mm Hg and 100 mmHg).

Samples removed from the reactor were also tested for the presence of monoclonal antibodies by two separate ELISA assays (Enzyme Linked Immunoabsorbent Assay). The first assay detected the presence of mouse immunoglobulin and consists of the following: unlabeled goat anti-mouse immunoglobulin is bound to microtiter plates overnight at 4° C. The plates are washed and then blocked within 0.1% solution of bovine serum albumin to reduce non-specific binding. After an additional wash, the sample is added and incubated for 2 hrs. at room temperature. After washing, labeled goat anti-mouse immunoglobulin (labeled with alkaline phosphatase) is added for an additional 2 hr. incubation. The latter material is washed off and p-nitrophenyl phosphate is added as a substrate and incubated for 30 min. at room temperature. The optical density of the colored reaction is read with a microtiter optical reader at 410 nm. The second ELISA assay involves specific recognition of the human hepatoma antigen against which mice were immunized for preparation of this hybridoma. In this case, the hepatoma antigen is bound at 4° C. overnight to the microtiter plates and all successive steps are the same as above. Substantial amounts of monoclonal antibody were detected by both assays in the effluent medium flowing from the reactor. Levels the same or greater than found in conditioned media from conventional culture of the hybridoma cells were shown. These results, indicate long-term sustained production of the specific monoclonal antibody by cells maintained at high density in the M-SMR system. At the conclusion of the run, approximately $2 \times 10^8$ viable cells were recovered.

EXAMPLE 2

A large scale static maintenance reactor (SMR) with a working volume of approximately 2 liters, as shown in FIGS. 3-5, was used to maintain an anchorage-dependent cell line for a period of about two months. The reactor vessel shell consisted of a 6-inch long, 6-inch diameter cylindrical Pyrex glass pipe end cap (Corning #72-6300). The high and low porosity tubes were constructed of the same material and had the same diameters as used in Example 1 but consisted of an array of 12 low porosity tubes and 9 high porosity tubes. One hundred ten to 120 feet of silicone rubber tubing as used in Example 1 was wound randomly around these porous tubes. During operation, a pressure drop of approximately 2 lbs/in$^2$ was used across this silicone rubber tubing for a flow of approximately 10 mls of gas/min.

The AG1523 human foreskin fibroblast cell line used in this example was obtained from the Institute for Medical Research, Camden, NJ at passage three. These cells were grown in T flasks and roller bottles in accordance with the procedure described in U.S. Pat. No. 4,273,871, the disclosure of which is incorporated herein by reference. Larger numbers of cells were produced in a 4-liter microcarrier reactor system as described in U.S. Pat. No. 4,335,215, the disclosure of which is incorporated herein by reference. After a cell density of $7.0 \pm 0.6 \times 10^6$ cells/ml was obtained, the cells still attached to the microcarriers (polyacrylamide Bio-Carriers®, BioRad Laboratories, Richmond, CA) were mixed with additional Bio-Carriers to provide a total settled volume of approximately 1800 mls. This thick slurry was pumped into the static maintenance reactor from the bottom while air was removed from an upper port. Additional matrix material, consisting of Sephadex G-50 chromatography beads, was used to completely fill the reactor. During the filling operation, excess liquid was allowed to flow out of the low porosity tubes into a medium supply manifold and out to a discard vessel. After the total reactor volume was solidly packed with matrix material containing the approximately $2.8 \times 10^{10}$ cells, a pressure overflow vessel was attached to an upper port and partially filled with Sephadex G-50 matrix slurry. This vessel was sealed with a 5 lb/in$^2$ check valve provided to prevent overpressurization of the reactor. Medium flow was then established through the reactor from the low porosity tubes to the high porosity tubes and out through an exterior manifold containing an INGOLD pH electrode into an effluent holding vessel. Initially, approximately 4 liters fresh medium were pumped over a 2 hr period to saturate the entire matrix and cells with fresh medium. Dulbecco's modified MEM medium with 4.5 grams/liter glucose supplemented with 6% fetal bovine serum was tially throughout the length or width of said matrix and perfusing said nutrient medium through the walls of said porous tube into said matrix, (c) withdrawing expended nutrient medium and cell product from said matrix by perfusing through the walls of at least one second porous tube disposed in said chamber substantially throughout the length or width of said matrix and passing said spent medium and cell product through an external outlet in said reactor, said second porous tube having a pore size larger than the pore size of said first porous tube, wherein the pore size of the first porous tube is from about 0.2 to about 5μ and wherein the pore size of the second porous tube is from about 10μ to about 150μ and said first and second porous tubes having closures at their ends within said chamber which are distal to the exterior culture medium inlet and outlet means, and (d) supplying oxygenated gaseous medium for said cells by perfusing into said chamber through the walls of at least one selectively-permeable tubular membrane disposed in said matrix substantially throughout the expanse of said matrix and having openings at both ends of its lumen for inlet and outlet of said gas to and from the outside of said reactor.

2. The method of claim 1 in which said second porous tube is concentric to said first porous tube.

3. The method of claim 1 in which a plurality of first porous tubes and a plurality of second porous tubes are disposed in substantially parallel relationship to each other in said matrix.

4. The method of claim 1 in which the semi-rigid matrix comprises a packed volume of polymeric approximately spherical microcarriers having a diameter of from about 30μ to about 400μ.

5. The method of claim 1 in which the animal cells are mammalian hydriboma cells and the cell product is monoclonal antibody produced by said cells.

6. The method of claim 1 in which the animal cells are mammalian fibroblast cells and the cell product has angiogenic or plasminogen activator activity.

7. Apparatus for maintaining animal cells in vitro in a substantially arrested state of proliferation with continuous secretion of cell product which comprises a housing, a chamber within said housing for holding cells in a semi-rigid matrix of finely divided particles with interstices for passage of fluid culture media, external culture medium inlet and outlet means disposed in a wall in said housing, said inlet means being in fluid communication with at least one first porous tube disposed substantially throughout the length or width of said chamber, said outlet means being in fluid communication with at least one second porous tube disposed substantially throughout the length or width of said chamber, external gas inlet and outlet means disposed in a wall in said housing and in gaseous communication with a selectively-permeable membrane disposed substrantially throughout the expanse of said chamber, said first and second porous tubes having closures at their ends within said chamber which are distal to the external culture medium inlet and outlet means, and said second porous tube having a pore size larger than the pore size of said first porous tube, wherein the pore size of the first porous tube is from about 0.2 to abut 5μ and wherein the pore size of the second porous tube is from about 10μ to about 150μ.

8. The apparatus of claim 7 in which said second porous tube is concentric to said first porous tube.

9. The apparatus of claim 7 in which a plurality of second porous tubes and a plurality of first porous tubes are disposed in substantially parallel relationship to each other in said matrix.

* * * * *